United States Patent
Vendrell Vila et al.

(10) Patent No.: US 12,178,688 B2
(45) Date of Patent: Dec. 31, 2024

(54) SANITARY TAMPON

(71) Applicant: Ramón Vendrell Vila, Barcelona (ES)

(72) Inventors: Ramón Vendrell Vila, Barcelona (ES); Ramon Font Caselles, Barcelona (ES)

(73) Assignee: Ramón Vendrell Vila, Barcelona (ES)

( * ) Notice: Subject to any disclaimer, the term of this patent is extended or adjusted under 35 U.S.C. 154(b) by 385 days.

(21) Appl. No.: 17/794,144

(22) PCT Filed: Feb. 10, 2021

(86) PCT No.: PCT/ES2021/070093
§ 371 (c)(1),
(2) Date: Jul. 20, 2022

(87) PCT Pub. No.: WO2021/160912
PCT Pub. Date: Aug. 19, 2021

(65) Prior Publication Data
US 2023/0051364 A1 Feb. 16, 2023

(30) Foreign Application Priority Data
Feb. 11, 2020 (ES) .............................. ES202030220U

(51) Int. Cl.
*A61F 13/20* (2006.01)
*A61F 13/00* (2024.01)
(Continued)

(52) U.S. Cl.
CPC ........ *A61F 13/2071* (2013.01); *A61F 13/206* (2013.01); *A61L 15/40* (2013.01); *A61F 2013/15983* (2013.01)

(58) Field of Classification Search
CPC ................ A61F 13/2071; A61F 13/206; A61F 2013/15983; A61L 15/40
See application file for complete search history.

(56) References Cited

U.S. PATENT DOCUMENTS 2,099,931 A * 11/1937 Fourness ................. A61F 13/34
604/375
3,971,379 A * 7/1976 Chatterjee ............. A61F 13/202
428/326
(Continued)

FOREIGN PATENT DOCUMENTS

DE 202019102949 U1 6/2019
ES 1 160 610 U 7/2016
WO WO-2007078413 A1 * 7/2007 ............. A61F 13/20

OTHER PUBLICATIONS

International Search Report mailed Jun. 25, 2021, in corresponding to International Application No. PCT/ES2021/070093; 7 pages.
(Continued)

*Primary Examiner* — Guy K Townsend
(74) *Attorney, Agent, or Firm* — Maier & Maier, PLLC

(57) ABSTRACT

A sanitary tampon that includes a body of generally cylindrical shape provided with a rounded front end in the insertion direction of the tampon and with a rear end from which an extraction cord protrudes; the body including an absorbent core, rectangular, with two major sides and two minor sides, covered with an absorbent sheet of non-woven fabric, and wound in the longitudinal direction and pressed together with said absorbent sheet, its major sides being oriented towards the front and rear ends of the body of the tampon and the tampon being made entirely of natural materials.

5 Claims, 5 Drawing Sheets

(51) Int. Cl.
*A61L 15/40* (2006.01)
*A61F 13/15* (2006.01)

(56) References Cited

U.S. PATENT DOCUMENTS

| | | | | |
|---|---|---|---|---|
| 4,274,412 A * | 6/1981 | Austin | A61L 15/28 | 604/377 |
| 5,709,774 A * | 1/1998 | Naieni | A61L 15/28 | 162/65 |
| 6,063,981 A * | 5/2000 | Wehner | A61F 13/51462 | 604/385.01 |
| 6,599,521 B1 * | 7/2003 | Resheski-Wedepohl | A61F 13/8405 | 424/443 |
| 8,845,837 B2 * | 9/2014 | Tomsovic | A61F 13/2068 | 156/196 |
| 11,071,656 B2 * | 7/2021 | Semidey-Flecha | A61F 13/2028 | |
| 2002/0040210 A1 * | 4/2002 | Luccio | A61L 15/42 | 604/367 |
| 2003/0073970 A1 * | 4/2003 | Suga | A61F 13/5518 | 604/385.18 |
| 2006/0167429 A1 * | 7/2006 | Denti | A61F 15/001 | 604/385.17 |
| 2007/0049887 A1 * | 3/2007 | Miura | A61L 15/46 | 604/367 |
| 2007/0142804 A1 * | 6/2007 | Bernard | A61L 15/225 | 604/374 |
| 2008/0275411 A1 * | 11/2008 | Hughes | A61F 13/2051 | 604/358 |
| 2009/0199349 A1 * | 8/2009 | Weinstein | D06M 15/263 | 8/120 |
| 2010/0042064 A1 * | 2/2010 | Kondo | A61F 13/20 | 604/385.02 |
| 2010/0152642 A1 * | 6/2010 | Kim | A61F 13/42 | 604/385.18 |
| 2012/0011462 A1 | 1/2012 | Westerman et al. | | |
| 2013/0158134 A1 * | 6/2013 | Martin | A61K 47/46 | 604/367 |
| 2014/0115845 A1 * | 5/2014 | Tomsovic | A61F 13/2071 | 28/118 |
| 2017/0246042 A1 * | 8/2017 | Ferrer | A61F 13/26 | |
| 2023/0051364 A1 * | 2/2023 | Vendrell Vila | A61F 13/206 | |

OTHER PUBLICATIONS

Written Opinion of the International Searching Authority mailed Jun. 25, 2021, in corresponding to International Application No. PCT/ES2021/070093; 5 pages.

* cited by examiner

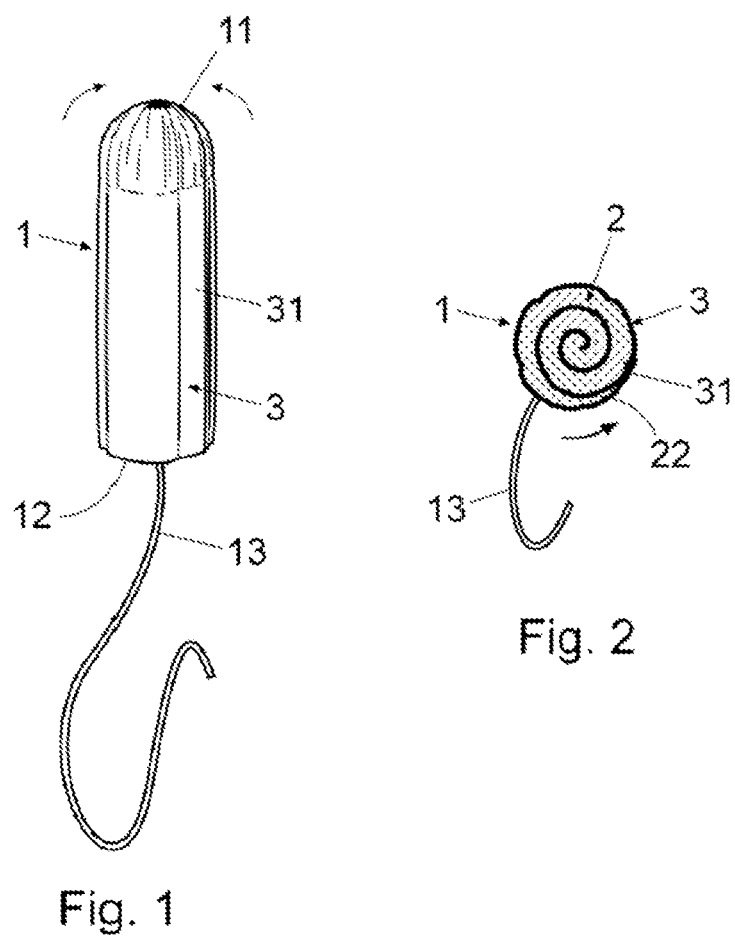

SANITARY TAMPON

TECHNICAL FIELD

This invention is applicable in the field of feminine sanitary pads, and more specifically sanitary tampons.

BACKGROUND

Utility model ES 1 160 610 U describes a tampon applicable in feminine hygiene that is of the type comprising: an absorbent body, substantially cylindrical, radially compressed and formed by a strip of absorbent material, rectangular in shape, wound over itself; said absorbent body having: a front end in the insertion direction of the tampon into the vagina; a rear end from which an extraction cord emerges and a side surface.

Document US2012011462 describes a menstrual tampon, with a structure similar to that of utility model ES 1 160 610 U, which includes a body that comprises: an absorbent material made up of a liquid absorbent sponge, a wrapping material made up of a liquid-permeable sheet material and adapted to wrap the absorbent material; and a cord for removing the tampon from the vaginal cavity.

The aforementioned background has characteristics aimed at preventing the absorbent fibers from coming into contact with the user's body, such fibers being able to adhere to the body and cause irritation or difficulties in removing the tampon.

In said background, the absorbent body is made up of a first sheet of non-woven fabric, of absorbent material, arranged on the absorbent core before winding and shaping of the tampon.

Shaping of the aforementioned tampons, by means of joint winding of the absorbent core and the absorbent sheet, has two drawbacks: the first drawback is the difficulty in forming the rounded front end of the tampon, due to the thickness formed in said area by the absorbent core during joint winding with the absorbent sheet; the second drawback is that during said winding there is a retraction, in the longitudinal direction, of the absorbent sheet with respect to the absorbent core, which causes that, upon completion of the winding, the fibers of the end of the absorbent core slightly protrude with respect to the end of the absorbent sheet, thus being exposed and being able to adhere to the user's body.

In the case the aforementioned utility model ES 1 160 610 U, these fibers are hidden by means of a polypropylene fastening strip, which is fixed by heat on the outer surface of the absorbent body, once wound.

This solution prevents the core protruding fibers from contacting the user, but has the drawback of including a plastic material in the tampon that entails environmental problems and a high risk of allergy or irritation for the user.

Therefore, the technical problem that arises is the development of a sanitary tampon that eliminates the problems derived from the use of plastic materials and that solves the aforementioned drawbacks, related to the rounded shape of the tampon front end and the unwanted exposure of the tampon absorbent core fibers after winding.

SUMMARY

The sanitary tampon of the present invention is of the type described in the preamble of the claim 1 and comprises: a body of generally cylindrical shape, laterally pressed and provided with a rounded front end in the insertion direction of the tampon, and a rear end from which an extraction cord protrudes; said body comprising a rectangular absorbent core with two major sides and two minor sides; said absorbent core being covered with an absorbent sheet of non-woven fabric, wound in a longitudinal direction and pressed together with said absorbent sheet, its major sides facing the front and rear ends of the tampon body.

To solve the problems raised and, according to the invention, the tampon is made entirely of natural materials and does not include any type of plastic or synthetic material.

Specifically, and preferably, the tampon is made entirely of organic cotton.

The absorbent sheet is wound on the absorbent core covering its major sides and its major faces.

To facilitate the rounded shaping of the front end of the tampon, one of the ends of the absorbent sheet forms a skirt that protrudes with respect to one of the major sides of the absorbent core, so that once the absorbent core and absorbent sheet have been wound and pressed, said skirt forms the rounded front end of the tampon body.

In this way, the shaping area of the rounded front end does not have the thickness of the absorbent core, and the mentioned drawback is avoided.

Between the successive turns of the skirt there is a hollow space, in the form of a spiral, which facilitates the folding and pressing of the skirt, and the shaping of said rounded front end of the tampon.

According to the invention, said absorbent core has a shorter length than the absorbent sheet, so that said absorbent sheet comprises an end section that protrudes through the minor side of the absorbent core that remains outside the body of the tampon once wound; and that closes said minor side on the tampon body itself, covering it completely.

According to the invention, it is also envisaged that the absorbent sheet comprises an end section that protrudes through the minor side of the absorbent core that remains inside the tampon body once wound and an end section that protrudes through the minor side of the absorbent core that remains on the outside of the tampon body once wound; and that closes said minor side on the tampon body itself, covering it completely. Said protruding end sections comprising a slanted side or a side having a slanted segment The end section that protrudes through the minor side of the absorbent core that remains on the outside of the body of the tampon once wound, has a suitable length to compensate for the retraction produced by the joint winding of the absorbent sheet and the absorbent core, and loosely cover the end of the absorbent core, preventing its fibers from being exposed and from coming into contact with the user.

The fixation of the absorbent sheet on the core is preferably carried out by pressing, avoiding the use of additional plastic material elements for fixing and closing or finishing the tampon body.

BRIEF DESCRIPTION OF THE DRAWINGS

To complement the description that is being made and in order to facilitate understanding of the characteristics of the invention, the present specification is accompanied by a set of drawings in which, by way of illustration and not limitation, the following has been represented:

FIG. 1 shows an elevation view of an embodiment of a sanitary tampon according to the invention, once wound and pressed.

FIG. 2 shows a plan view of the tampon of FIG. 1, sectioned along a horizontal plane.

DETAILED DESCRIPTION OF THE EMBODIMENTS

Figure 3:
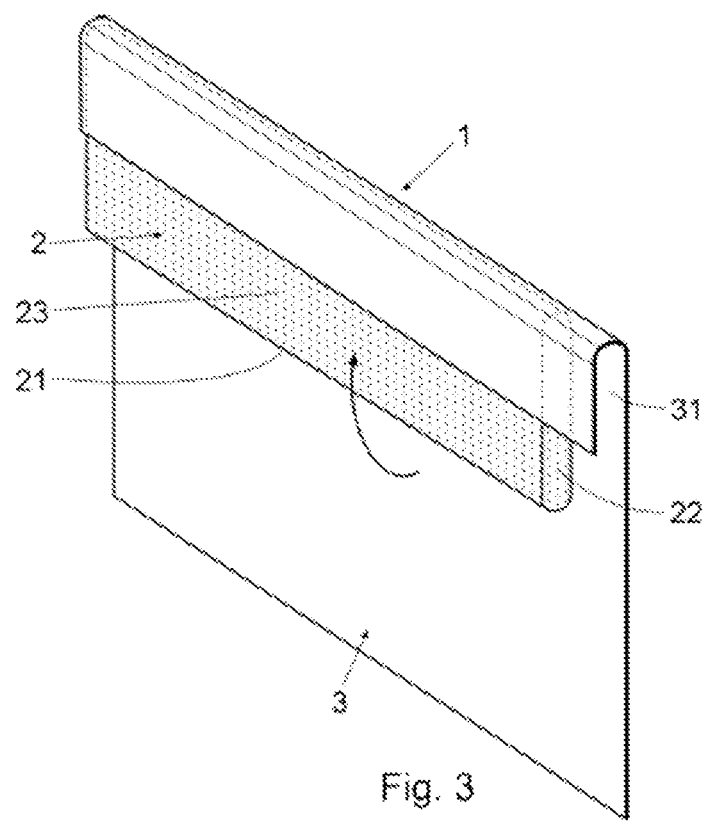
FIG. 3 shows a perspective view of the absorbent core in an extended position when covered with a rectangular absorbent sheet, according to an embodiment of the present invention.

The sanitary tampon shown in FIG. 1, comprises a body (1) of generally cylindrical shape, provided with a rounded front end (11) in the insertion direction, and a rear end (12) from which an extraction cord (13) protrudes.

As can be seen in FIG. 2, the body (1) of the tampon comprises an absorbent core (2), covered with an absorbent sheet (3) of non-woven fabric, and wound in a longitudinal direction and pressed together with said absorbent sheet (3).

In an exemplary embodiment of the present invention, the absorbent sheet (3) is made of a hydroentangled non-woven fabric, to prevent the fabric fibers of the absorbent sheet (3) from adhering to the vaginal wall of a user and cause irritations or difficulties in removing the tampon.

The tampon is made entirely of natural materials, preferably organic cotton, and does not include any type of plastic or synthetic material.

As shown in FIG. 3, the absorbent core (2) has a rectangular configuration, with two major sides (21) oriented towards the front (11) and rear (12) ends of the body (1) once the tampon has been shaped, and two minor sides (22).

The absorbent sheet (3) can have different configurations.

In one embodiment, as shown in FIG. 3, the absorbent sheet (3) has a rectangular configuration and the absorbent core (2) has a shorter length than the absorbent sheet (3), said absorbent sheet (3) comprising an end section (31) that protrudes with respect to one of the minor sides (22) of the absorbent core (2).

The protruding end section (31) of the absorbent sheet (3) has a suitable length to compensate for the retraction produced by the winding of the absorbent sheet (3) and the absorbent core (2), and to loosely cover the end of the absorbent core (2), preventing the fibers of the absorbent core (2) from being exposed and being able to come into contact with the user.

In another embodiment, according to the invention, the absorbent core (2) has a shorter length than the absorbent sheet (3), and said absorbent sheet (3) comprises two end sections (31, 33) that protrude with respect to the two minor sides (22) of the absorbent core (2). The end section (33) protrudes through the minor side (22) of the absorbent core that remains inside the body (1) once wound and the end section (31) protrudes through the minor side (22) of the absorbent core that remains on the outside of the body (1) once wound, and closes said minor side (22) on the body (1) itself, totally covering the material of the absorbent core (2).

Figure 5:
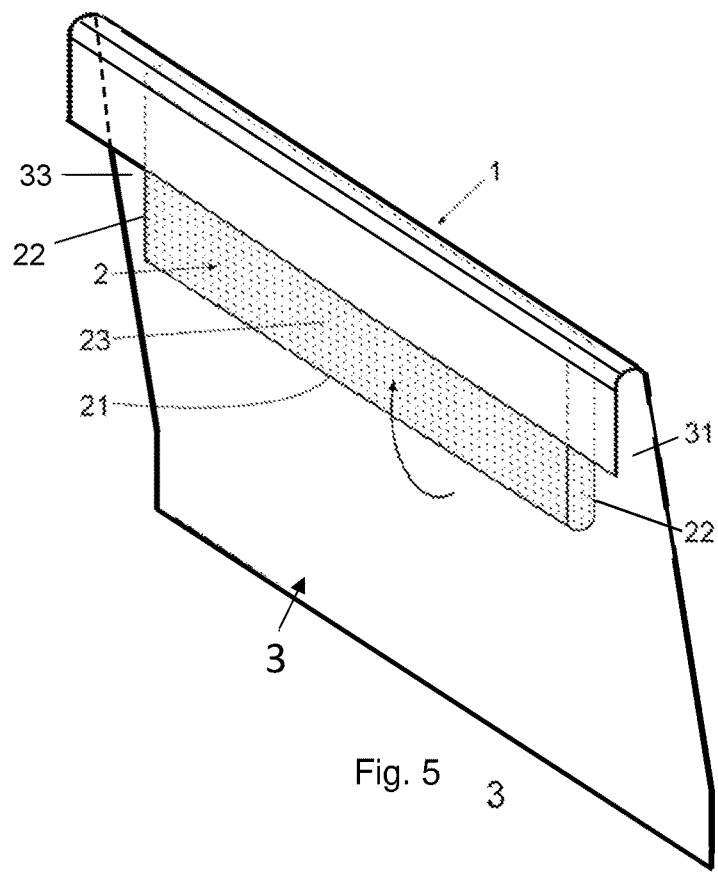
FIG. 5 shows a perspective view of the absorbent core in an extended position when covered with an absorbent sheet that has end sections with a slanted side.
Figure 6:
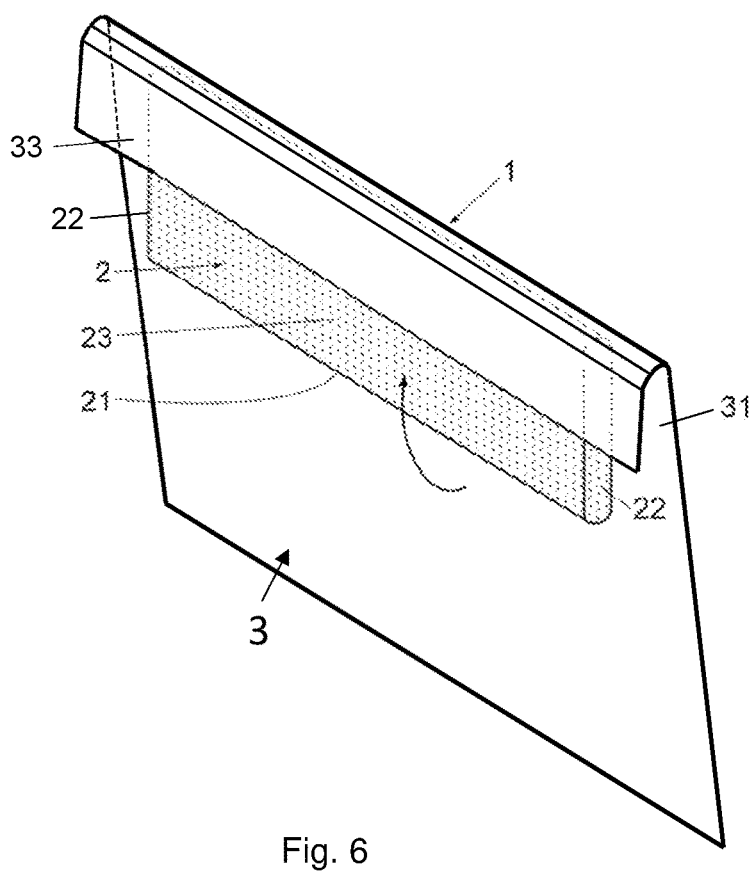
FIG. 6 shows a perspective view of the absorbent core in an extended position when covered with an absorbent sheet that has end sections with one side having a slanted segment.
Figure 7:
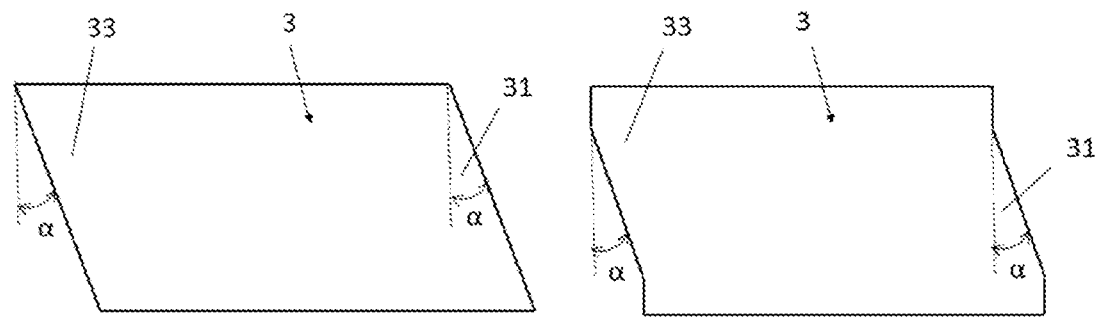
FIG. 7 shows different configurations of the absorbent sheet, according to different embodiments of the present invention.
Figure 8:
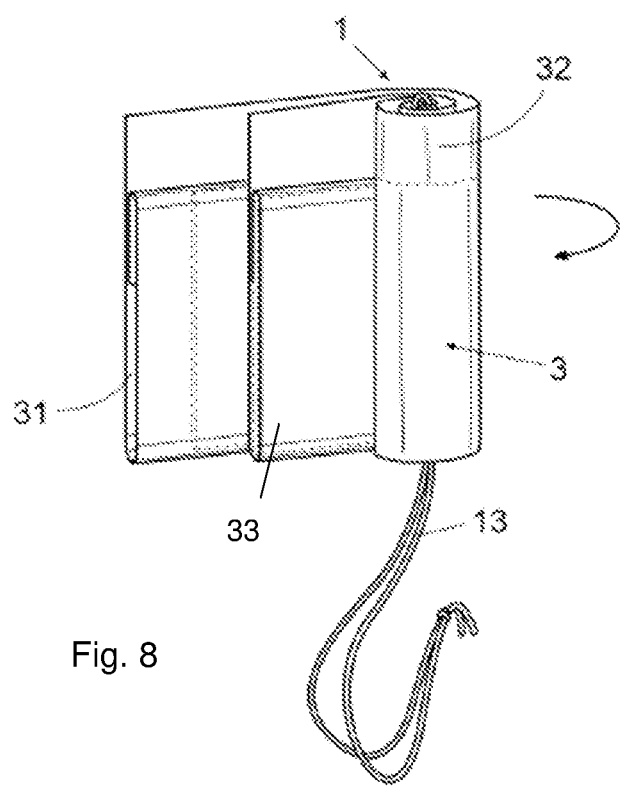
FIG. 8 shows a perspective view of the core, covered with the absorbent sheet, once folded by an off-centered area and further away from the end of the absorbent sheet that defines the protruding end section, during its joint winding in the longitudinal direction and prior to the pressing and shaping of the tampon shown in FIG. 1.
Figure 9:
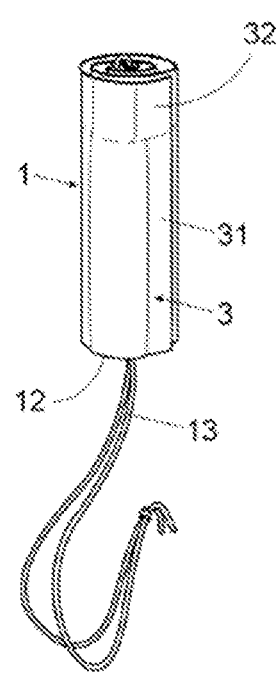
FIG. 9 shows a perspective view of the core, covered with the absorbent sheet, once folded by an off-centered area and further away from the end of the absorbent sheet that defines the protruding end section, during its joint winding in the longitudinal direction and prior to the pressing and shaping of the tampon shown in FIG. 1.

As shown in FIGS. 5 and 6, in this embodiment the absorbent sheet (3) has a configuration such that the end sections (31, 33) that protrude with respect to the two minor sides (22) of the absorbent core (2) comprise each one a slanted side or a side having a slanted segment. Said slanted side or slanted segment having a slanted angle α of between 10 degrees and 20 degrees.

Such a configuration is favorable for obtaining a tampon with a continuous outer surface, free of protruding ends, once wound, and for reinforcing the hold of the tampon in the wound-up position.

Figure 10:
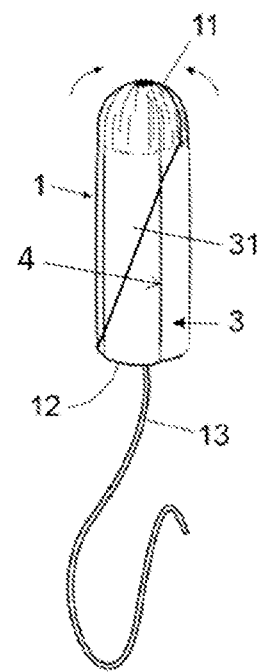
FIG. 10 shows an elevation view of the embodiment of the tampon of FIG. 6, once wound and pressed.

The absorbent core (2) and the absorbent sheet (3), once wound, are radially pressed. The resulting tampon has longitudinal grooves (4), as shown in FIG. 10, caused by pointed pressure jaws. The configuration of the end sections (31, 33) allows the slanted sides or sides having slanted segments to be positioned between at least two of these longitudinal grooves (4), reinforcing the hold of the absorbent sheet (3) in a wound-up position and preventing that the end (31) that protrudes from the minor side (22) of the absorbent core that remains on the outside of the body (1) is loose, once wound up.

Figure 4:
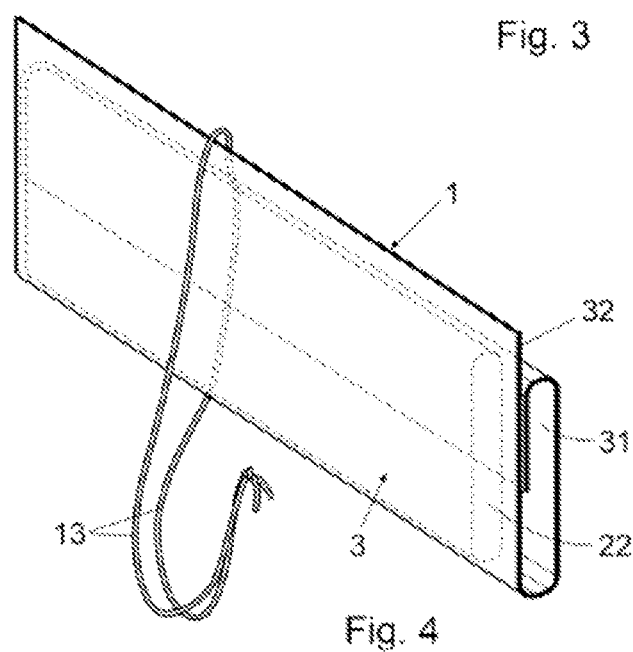
FIG. 4 shows a perspective view of the absorbent core in an extended position when covered with a rectangular absorbent sheet, according to an embodiment of the present invention.

As shown in FIG. 4, once the absorbent sheet (3) has been wound over the absorbent core (2), covering its major sides (21) and its major faces (23), one of the longitudinal ends of the absorbent sheet (3) defines a skirt (32) that protrudes with respect to one of the major sides (21) of the absorbent core (2).

When winding the absorbent core (2) and the absorbent sheet (3), as shown in FIG. 5, they adopt the cylindrical shape of the tampon shown in FIG. 6, and at the end of the winding, the end section (31) of the absorbent sheet (3) closes the minor side (22) of the core on the body (1) itself, completely covering it and preventing its fibers from being exposed to the outside.

During said winding, the skirt (32) of the absorbent sheet (3) defines a hollow spiral and, during the pressing of the tampon, said skirt (32) forms the rounded front end (11) of the tampon.

Once the nature of the invention has been sufficiently described, as well as a preferred embodiment, it is stated for the appropriate purposes that the materials, shape, size and arrangement of the elements described may be modified, as long as this does not involve an alteration of the essential features of the invention that are claimed below.

The invention claimed is:

1. A sanitary tampon, made entirely of natural materials and not including any type of plastic or synthetic material, comprising: a body of generally cylindrical shape provided with a rounded front end in a direction of insertion of the tampon and a rear end from which an extraction cord protrudes; said body comprising an absorbent core that is rectangular, with two major sides and two minor sides; said absorbent core being covered with an absorbent sheet of non-woven fabric, and wound up in a longitudinal direction and pressed together with said absorbent sheet, the major sides oriented towards the front and rear ends of the tampon body; said absorbent sheet comprising an end section that protrudes through the minor side of the absorbent core that remains inside the body once wound and an end section that protrudes at least on the minor side of the absorbent core that remains outside of the body once wound, and that closes said minor side on the body itself, totally covering the material of the absorbent core;

wherein the end sections of the absorbent sheet comprise a slanted side or a side having a slanted segment.

2. The sanitary tampon according to claim 1, wherein the absorbent sheet of non-woven fabric is a hydroentangled non-woven fabric sheet.

3. The sanitary tampon according to claim 1, wherein the absorbent sheet is wound on the absorbent core covering its major sides and its larger faces; one of the ends of the absorbent sheet defining a skirt that protrudes with respect to one of the major sides of the absorbent core and that, once wound and pressed, forms the rounded front end of the tampon body.

4. The sanitary tampon according to claim 1, wherein said slanted side or slanted segment has a slanted angle $\alpha$ of between 10 degrees and 20 degrees.

5. The sanitary tampon according to claim 1, wherein the sanitary tampon is entirely made of organic cotton.

* * * * *